United States Patent [19]
Rouquerol et al.

[11] Patent Number: 4,967,591
[45] Date of Patent: Nov. 6, 1990

[54] APPARATUS, APPLICATION AND METHOD OF MAKING A GAS FLOW REGULATOR OPERATING AT A VERY LOW FLOW RATE AND AT SONIC VELOCITY FOR MEASURING GASEOUS ADSORBTION AND DESORBTION

[75] Inventors: Jean Rouquerol; Lou J. Davy, both of Marseille, France

[73] Assignee: Centre National de la Recherche Scientifique-C.N.R.S., Paris, France

[21] Appl. No.: 390,212

[22] Filed: Aug. 7, 1989

[30] Foreign Application Priority Data

Aug. 12, 1988 [FR] France ................. 88 10972

[51] Int. Cl.$^5$ ........................................... G01N 15/08
[52] U.S. Cl. ........................................................ 73/38
[58] Field of Search .................. 73/3, 38, 866; 29/407

[56] References Cited

U.S. PATENT DOCUMENTS

| | | | |
|---|---|---|---|
| 2,729,969 | 1/1956 | Innes | 73/38 |
| 3,139,747 | 7/1964 | Ferrell et al. | 73/38 |
| 3,211,007 | 10/1965 | Atkins | 73/865.5 |
| 3,255,122 | 6/1966 | Constabaris et al. | 73/38 |
| 3,707,870 | 1/1973 | Herve et al. | 73/38 |
| 4,489,593 | 12/1984 | Pieters et al. | 73/38 |

FOREIGN PATENT DOCUMENTS 1515676  1/1968  France .

Primary Examiner—Robert Raevis
Attorney, Agent, or Firm—Dvorak and Traub

[57] ABSTRACT

The gas flow regulator apparatus of the invention comprises a tube made of ductile metal which is crushed over a short portion of its length so that the inside wall of said tube makes contact with itself, and the tube is mounted in connection means for providing sealing around the tube and for mounting it in any equipment for measuring gaseous adsorbtion and desorbtion, in such a manner that the tube ensures that the equipment is continuously fed with gas at a very low flow rate lying in the range 0.025 mm$^3$/sec to 25 mm$^3$/sec at sonic velocity and regardless of any varying back pressure.

10 Claims, 2 Drawing Sheets

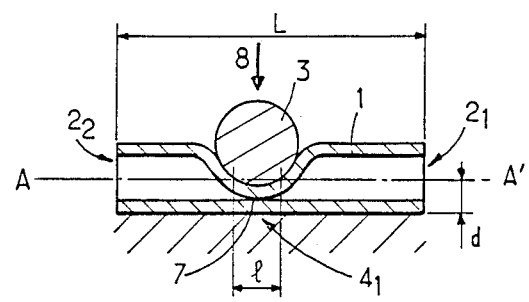
Fig_1a
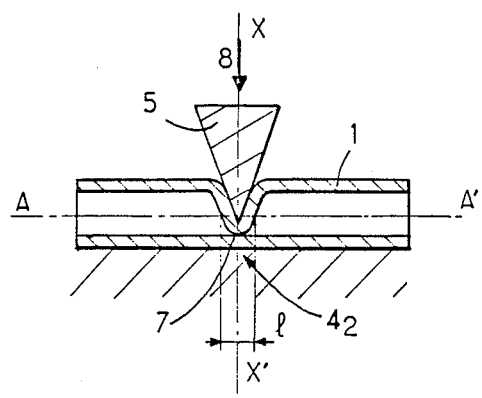
Fig_1b
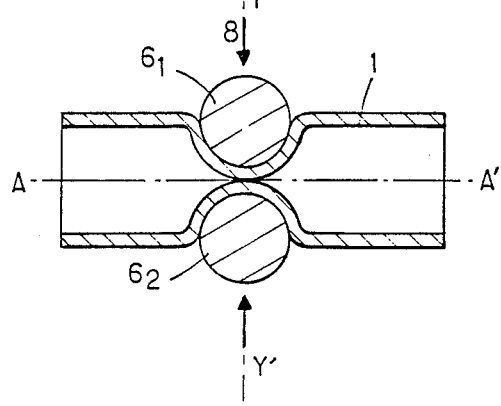
Fig_1c
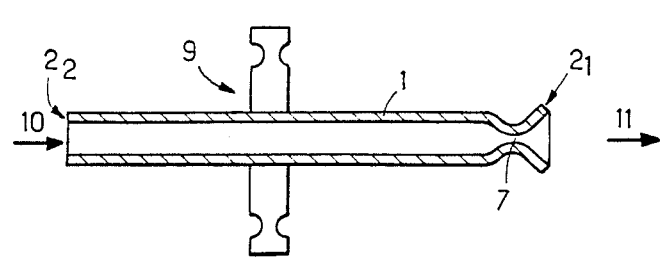
Fig_2

APPARATUS, APPLICATION AND METHOD OF MAKING A GAS FLOW REGULATOR OPERATING AT A VERY LOW FLOW RATE AND AT SONIC VELOCITY FOR MEASURING GASEOUS ADSORBTION AND DESORBTION

The present invention relates to apparatus, applications, and methods of making a gas flow regulator capable of delivering a very low flow rate at sonic velocity for measuring gaseous adsorbtion and desorbtion.

The technical field of the invention is manufacturing equipment for volumetric measurement of gas. One application of the invention is determining the specific area of an adsorbant by continuous and very accurate injection of an adsorbable gas.

It is well known that the adsorbtion of a gas (i.e. retention of the gas on a surface) by porous or divided solids (such as catalysts, adsorbants for purifying or separating gases or liquids, pigments, binders, fillers for rubber or plastic material, plant-dusting powders, etc. . . .) is a phenomenon which is very widely used for characterizing the surface state, the degree of division, and the porosity of these solids. The gases used for performing such characterizations are either chemically adsorbed (in particular $H_2$, CO, $NH_3$, $O_2$, and various hydrocarbons) or else they are physically adsorbed (in particular $N_2$, Ar, Kr, $CO_2$, and $H_2O$). The quantification and exploitation of the adsorbtion phenomenon always requires more or less complete adsorbtion isotherms to be determined, i.e. curves which specify, at a given temperature, the equilibrium quantity of adsorbed gas as a function of the pressure of the gas over the adsorbant. When the gas is capable of giving rise to three-dimensional condensation at the temperature of the experiment, it is conventional to express the equilibrium pressure relative to the saturated vapor pressure at that temperature and to refer to a relative equilibrium pressure.

The quantity of gas adsorbed is commonly determined either by volumetric analysis of the gas, or by gravimetric analysis, or else by measuring changes in the concentration of the adsorbable gas in a vector gas by means of a katharometer. These three methods are commonly used for discontinuously determining a limited number of points on the adsorbtion isotherm. Attempts have been made over a long period of time to avoid the limitations of this discontinuous procedure (suffering from limitations of resolution and limitations of experimental convenience) by using a procedure in which the adsorbable gas is injected slowly and continuously.

One such procedure has been used, in particular, by Mr. W. B. Innes, as described in the publication Analytical Chemistry, 1951, 23, pp. 759 to 763, but at a flow rate of about 66 $mm^3$ per second (under conditions of normal temperature and pressure) which turns out to be much too fast in most circumstances for obtaining conditions of quasi equilibrium, i.e. conditions such that the pressure measured "on the fly" above the adsorbant coincides at all times (within limits fixed in advance and depending on the desired quality of measurement, e.g. to within 1%) with the thermodynamic equilibrium pressure towards which the system would tend if the injection of additional adsorbable gas were to be stopped at the instant of measurement. This procedure of slow and continuous injection of adsorbable gas has been used with success in gravimetric analysis of adsorbtion, as described in the publication "Progress in Vacuum Micro Balance Techniques" vol. 3, published by C. Eyraud and Escoubes, pp. 83 to 92, in 1975, with a search for correct conditions of quasi equilibrium and with adsorbtion rates which are not constant but which are as low as 0.07 $mm^3$/sec, thus one thousand times smaller than in the previously-mentioned work. This procedure was used with volumetric analysis of adsorbtion as described in the "Revue Générale de Thermique" No. 171, 1976, pp. 257 to 241, and made it possible under certain conditions to obtain constant injection rates of adsorbable gas lying in the range 1.7 $mm^3$/sec to 3.4 $mm^3$/sec for the purpose of continuous tracing of nitrogen adsorbtion isotherms on silica gells. This continuous procedure has also been used in gravimetric analysis of adsorbtion for tracing adsorbtion-desorbtion isotherms of nitrogen or water vapor completely, as described in the journal Thermochimica Acta, 24, 1978, pp. 391 to 397.

Various patents have been taken out on the above-mentioned analysis methods and procedures, and also on equipment for applying these methods and procedures, and particular mention may be made of patents for discontinuous methods such as a patent filed by Micrometrics Instrument on 8 Apr. 1968 in the United States under Ser. No. 719562 and subsequently extended to France, an application filed by EURATUM on 10 Dec. 1969 under Luxembourg application No. 59979, and the application filed by Laboratoire des Ponts et Chaussées on 18 May 1983 under French application No. 8308242. For the continuous method, mention may be made of a patent application filed on 9 Sept. 1982 in the United States by Omicron Technology Corporation under Ser. No. 416164, and not extended to Europe, and which nevertheless claims both the general method and certain particular methods described in the earlier above-mentioned publications which set forth the state of the art.

The idea of adsorbtion at a very slow and possibly constant rate has attracted numerous researchers over many years since it would enable an adsorbtion isotherm to be traced continuously with an infinity of quasi-equilibrium points, thereby improving measurements, and in particular enabling specific area to be deduced with greater accuracy. Numerous tests have thus been performed and described since 1976 for improving this most advantageous and most desired method. However, the improvement obtained in measurement has, prior to the present invention, been constrained by the need to operate at adsorbtion rates lying in the range 0.03 $mm^3$/sec to 3 $mm^3$/sec (under condition of normal temperature and pressure, NTP) in order to ensure satisfactory quasi-equilibrium conditions. It is difficult, firstly to obtain such a flow rate, and secondly to keep it stable for the time required to perform an experiment (in the range 15 minutes to 15 hours), given variations in atmospheric pressure and the increase in the quasi-equilibrium pressure during adsorbtion, and finally, it is difficult to measure.

Various means have been used in the past for providing this low flow rate: high precision adjustable leakage valves such as those used for calibrating mass spectrometers, sintered metal powder filters, stretched capillary tubes (made of glass or metal), and diaphragms pierced by laser to have holes with a diameter of about 1 micrometer. However, in order to maintain a constant flow rate, in spite of downstream pressure varying over a range of 0 pascals to 40,000 pascals, all of these techniques require flow rate to be measured on a permanent basis (in a range of flow rates which is particularly difficult to measure), together with feedback for opposing any variation (by acting on an adjustable leakage valve or on the upstream pressure). A few patents have been filed in France for measuring these low gas flow rates, e.g. an application filed 19 May 1983 by Curadom under the No. 8308657, or an application filed 15 Sept. 1977 by Mr. R. Gsalder under the No. 7728534, or an application filed 29 Jun. 1977 by Mr. G. Samman under the No. 7719900. In addition, no commercially available equipment is capable of providing the performance characteristics required for accurate measurement of adsorbtion as described above: even the highest performance temperature regulator flow meters made by the Brook Division of Emerson Electric has a lowest measurement range of 0 $mm^3$/sec to 80 $mm^3$/sec with a detection threshold and accuracy of no better than ±0.8 $mm^3$/sec.

One known way of obtaining a constant low flow rate, even when the downstream pressure may be varying, is to provide a regulator in which the molecular velocity of the gas is sonic: to achieve this, it is known that the ratio of the upstream pressure to the downstream pressure on either side of the regulating orifice merely needs to be greater than some critical ratio, above which the flow rate is proportional to the diameter of the orifice and to the upstream pressure only. Sonic velocity micro flow rate gas flow regulators have thus been made by piercing a plate of stainless steel or some other material, including ruby, with a laser to have a hole whose diameter is less than 1 micrometer. Unfortunately, the resistance to gas flow set up by such orifices is too small to enable performance to be obtained which is accurate, stable in flow rate, and covering a small range of micro flow rates, since if the holes are small in diameter, the thickness of the material through which they are made is also small.

The problem posed is thus to be able to make a gas flow regulator operating at sonic velocity and enabling a mass flow rate to be obtained which is as low as 0.03 $mm^3$/sec and which is sufficiently stable to remain constant to within better than 1% accuracy at fixed constant upstream pressure with downstream pressure covering the range from vacuum to at least one-tenth of the upstream pressure.

A solution to the problem is provided by an apparatus comprising a gas flow regulator operating at a low flow rate and at sonic velocity and usable in any conventional equipment for measuring gaseous adsorbtion and desorbtion, the apparatus being characterized in that it is constituted by a small section tube of ductile metal, e.g. copper, having a small portion of its length crushed in such a manner that the inside wall of said tube makes contact with itself, said tube being mounted on connection means serving both to provide sealing around the tube and to mount the tube in the said equipment for measuring gaseous adsorbtion and desorption in such a manner as to enable the tube to provide a continuous feed of gas for said equipment at a very low flow rate regardless of the back pressure therein which may vary from vacuum to at least one-tenth of the upstream feed pressure.

Another solution to the problem posed is provided by a method of making a gas flow regulator that operates at a very low flow rate and at sonic velocity, the regulator being usable in any conventional equipment for measuring gaseous adsorbtion and desorbtion, operating at given utilization pressures, and into which a gas is to be injected at a selected very low flow rate, the method being characterized in that:

a small section tube of ductile metal, e.g. copper, is taken having a wall thickness which is sufficient to withstand said various utilization gas pressures;

said tube is mounted on connection means serving both to provide sealing around the tube and also to enable it to be mounted in said equipment, said means being mounted close to an end of said tube and at a sufficient distance therefrom to enable the following operations to be performed, which operations may alternatively be performed prior to mounting the tube in the connection means;

a short length of said tube is crushed between said connection means and the above-mentioned corresponding end;

said connection means is connected together with the tube to a known calibrated volumetric measuring apparatus, and a gas is applied at one end of the tube at a given calibration pressure, and, for example, the increase in pressure in the known volume into which the other end of the tube opens out is measured with the initial pressure of the volume being selected as a function of the desired calibration range and of the upstream pressure of the applied gas; and the flow rate obtained in this way is determined on a continuous basis and it is verified that the flow rate is constant and corresponds to not more than the selected value over the entire desired range of variation in downstream pressure during measurement, and if the verification fails the crushing operation is continued by slightly increasing the extent to which the tube is pinched, and calibration is verified again until a flow rate is obtained which is no greater than the desired flow rate given said initially selected utilization pressures.

The result is a novel method of making a new sonic velocity regulator capable of providing very low flow rates for measuring gaseous adsorbtion and desorbtion.

The advantages of such a method and such a regulator are numerous since they enable very highly accurate measurements to be performed over wide pressure ranges, and they make it possible to provide regulators in a manner which is very reliable, safe, and cheap. The starting material is easily found by using any type of ductile material such as copper which is the cheapest, but also silver or gold, and implementing the manufacturing method is easily done: only the calibration requires any precautions to be taken and this is done using conventional volume and pressure measuring apparatus. In addition, there is no a priori limit on the maximum restriction that such a clamped nozzle regulator can apply to the gas flow, nor is there is any maximum limit on the wall thickness of the tube wall, so it is possible to apply an upstream pressure of several MPa if necessary in order to extend the range of sonic conditions as a function of downstream pressure.

The use of such a regulator having a very low flow rate, i.e. 0.025 $mm^3$/sec to 25 $mm^3$/sec, and having good stability, thus advantageously replaces any type of prior flow meter as mentioned above, since such meters are highly sophisticated with electronic control and regulation and nevertheless have a limiting detection threshold by virtue of the way they are designed which is beneath the threshold that is desirable for performing good pressure measurements in continuous quasi-equilibrium for determining an adsorbtion isotherm.

Only regulators made by the method of the present invention satisfy these criteria. They also offer the possibility of making high performance measuring apparatus with which various very accurate and reliable measurement methods and procedures can be devised, e.g. for rapidly measuring specific area or for measuring gaseous desorbtion.

The following description is made with reference to the accompanying drawings which show non-limiting embodiments and implementations of the invention which are given purely by way of example since other embodiments and applications could be envisaged. In the drawings:

FIG. 1a is a section view through manufacturing means including a ball;

FIG. 1b is a section view through manufacturing means for crushing by means of a prism;

FIG. 1c is a section view through manufacturing means for crushing by means of one or two rollers;

FIG. 2 shows a regulator mounted on a flange;

Figure 3:
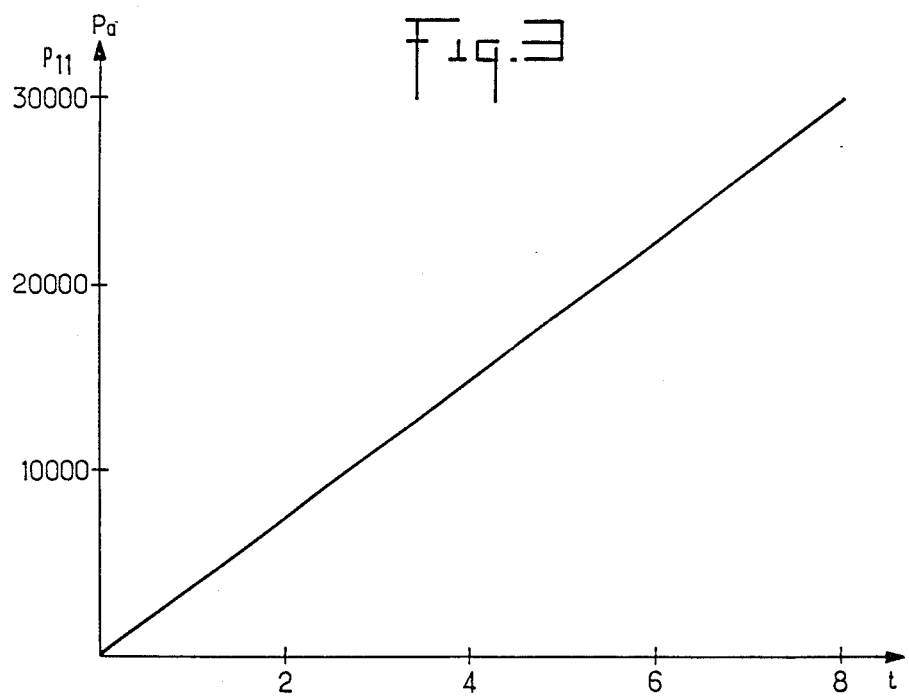
FIG. 3 is a graph showing one example of a pressure curve.

FIG. 1a is a section view of a small section tube made of ductile metal, e.g. copper but possibly also ductile steel, platinum, silver, or gold. The tube is of length L such that its two ends 2.1 and 2.2 can easily be connected to measuring apparatus as described with reference to FIGS. 2 and 4.

The tube 1 is placed in clamping means enabling a small portion 1 of its length to be crushed so that the inside wall of the tube comes practically into contact with itself and may leave a flow passage 7 with an area of less than one square micrometer. To do this, it is possible to place one side of the tube against a ball 3 which is larger in diameter than the width of the tube 1, or which has the same diameter if the tube is a cylinder (since other tubular sections could be envisaged), and to place the other side of the tube 1 against an anvil 4.1. The tube is then crushed using the ball which is moved towards the anvil 4.1 by any appropriate clamping means 8, until a distance d corresponding to the selected maximum sonic flow rate is reached, as determined using the calibration method described above. This distance is a function of the thickness of said tube (i.e. not more than twice the said thickness), of the utilization pressures used, and on the maximum desired flow rate. If necessary, the deformed portion is annealed between two clamping and calibrating operations in order to stabilize the resulting deformation.

FIG. 1b is a section view through second means for manufacturing a flow rate regulator of the invention by crushing: in this example, the tube 1 is pinched between a surface 4.2 on one side constituting an anvil and prism 5 on the other side, with an edge of the prism being moved towards the surface 4.2 by any appropriate means 8 as described with reference to FIG. 1a. The surface 4.2 may be arbitrary, providing its intersection with the plane XX' containing said edge of the prism and parallel to the direction of prism displacement is a convex line whose radius of curvature is greater than the radius of curvature of the tube 1. The advantage of using such crushing means including a prism is that the length l of tube pitched thereby is small, and the smaller this length, the smaller the flow section 7 and the greater the sonic operating range of the nozzle formed in this way.

FIG. 1c is a section view through another manufacturing means which crushes the tube 1 between a first roller 6.1 on one side and a second roller 6.2 on the other side. The second roller may be replaced by any abutment-forming surface whose intersection with the plane YY' passing through the axis of the first roller 6.1 and containing the direction in which the crushing displacement is performed is a convex line whose radius of curvature is greater than the radius of curvature of the tube 1. Any appropriate clamping means 8 serve to move the rollers 6.1 and 6.2 towards each other, after which the above-described calibration method is performed, as for the means shown in FIGS. 1a and 1b.

The three crushing means described above are not limiting and are given merely by way of example: the tube could also be crushed by an annular constriction set up by hydraulic pressure, or by circular displacement of a roller, or by various geometrical shapes such as four cylinders parallel to the axis of said tube.

FIG. 2 shows how a regulator made according to one of the methods described with reference to FIGS. 1a, 1b, or 1c, for example, can be mounted, said regulator being constituted by the tube 1 whose portion 7 has been crushed to constitute the sonic flow nozzle, together with appropriate connection means 9, e.g. an ultra-vacuum flange having metal seals. The flange 9 serves firstly to provide sealing around the tube 1 and secondly to enable the assembly to be mounted on any appropriate measurement circuit such as that described with reference to FIG. 4. The flange may be mounted before the operation of crushing the tube and at a sufficient distance from the end 2.1 to leave room for the clamping and crushing operations to take place.

The other end 2.2 is connected to a supply 10 of gas under pressure which is to be delivered at constant flow rate into an enclosure 11 in which measurements are made of volume, of pressure, and of adsorbtion. When the gas molecules flow along the nozzle 7 at subsonic velocity, the mass flow rate of the gas is given by:

$$dm/dt = k1 \times S7 \times k2 \ (P10 - P11)$$

where S7 is the smallest flow cross-section in the nozzle, k1 is a constant depending on the expansion factor of the gas, k2 is another constant, depending on the density of the gas upstream at pressure P10, and P11 is the outlet pressure from the nozzle 7. In theory, it is possible to eliminate, at least in part, the effect of a change in the downstream pressure P11 on the mass flow rate by imposing sonic conditions such that the molecules reach the speed of sound in the region 7 of the nozzle. To make this possible, the ratio P11/P10 of the downstream pressure divided by the upstream pressure must be below a critical threshold which, for air, is equal to 0.53. In this case, the mass flow rate can be written:

$$(k3 \times S7 \times P10)/T1$$

thus giving a constant flow rate at a given temperature T1 and a fixed upstream pressure P10. In order to make this highly reliable, given that other parameters must be capable of being selected as a function of the tests which are to be performed, the only quantity that can be varied freely is the section S7, and the method of the invention makes it possible to obtain very small values satisfactorily. In particular, it is possible with this method to select and obtain a maximum gas injection flow rate via the nozzle 7 into the volume 11 within the range 0.025 mm$^3$/sec to 25 mm$^3$/sec, with said flow rate remaining constant to within 1% while the downstream pressure P11 varies over a maximum range of 0 pascals to 100,000 pascals.

FIG. 3 shows an example of the pressure curve obtained by taking a flow rate regulator as described and made using the method of the present invention and mounting it on a continuous volumetric apparatus for performing adsorbtion and desorbtion measurements. The upstream pressure P10 feeding a regulator with nitrogen in the application chosen for this test was 350,000 pascals and the volume of the previously evacuated enclosure 11 into which the flow of gas was injected as described with reference to FIG. 2 was 25 cm$^3$. The curve of FIG. 3 gives the increase in pressure P11 as a function of time t expressed in hours. The curve is a good approximation to a straight line proving that the flow rate was indeed both constant and stable. In particular, the flow rate was 0.25 mm$^3$/sec and it remained constant to within a 0.5% for the upstream pressure P10 of 350,000 Pa and for variation in the downstream pressure P11 from 0 Pa to 30,000 Pa.

Other tests and implementations may be performed and any continuous gaseous adsorbtion and desorbtion measurement apparatus can be provided with a micro flow rate regulator in accordance with the characteristics and the method of the present invention.

Figure 4:
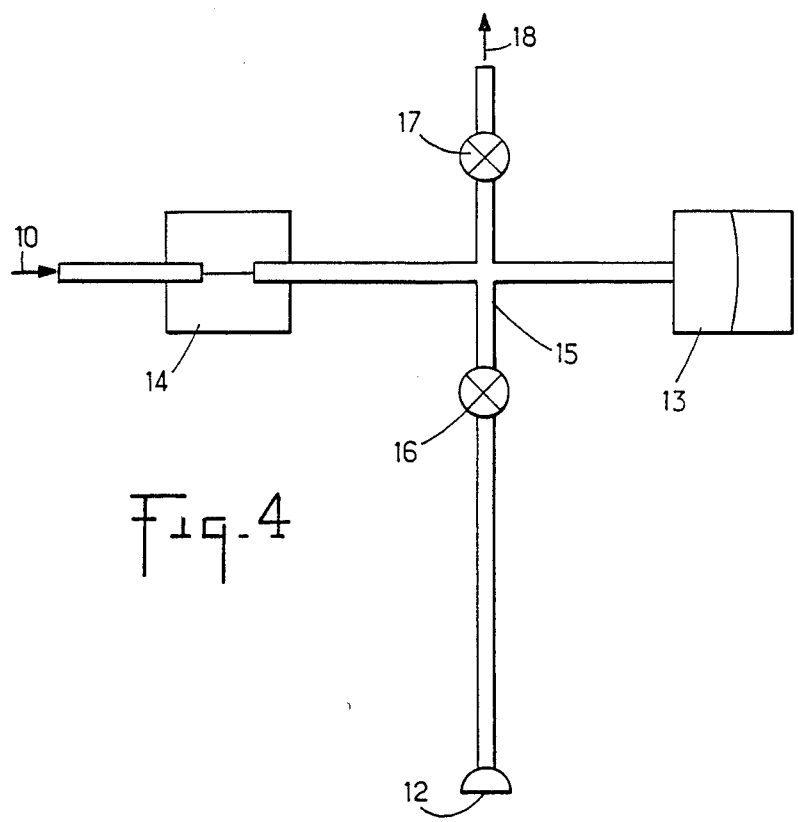
FIG. 4 is a diagram of an experimental set-up including a regulator in apparatus for measuring gaseous adsorbtion and desorbtion.

FIG. 4 is a diagram showing how a sonic regulator can be mounted in the simplest imaginable prior art apparatus for measuring gaseous adsorbtion and desorbtion. In conventional manner, this apparatus comprises:

a bulb 12 containing a sample of adsorbant material and maintained at a desired temperature (e.g. 77° K. for nitrogen adsorbtion in order to determine specific area by the BET (Brunauer-Emmett-Teller) method as described in the recommendations of the IUPAC (International Union of Pure and Applied Chemistry) for presenting gaseous adsorbtion data);

an absolute pressure sensor 13 for continuously recording the quasi-equilibrium pressure;

a regulator 14 fed with adsorbable gas at constant pressure 10 (which pressure should theoretically be not less than, and in practice should be greater than, the quotient of the maximum downstream pressure divided by the "critical ratio" corresponding to switching from subsonic conditions to sonic conditions for the gas in question, said regulator 14 or constant flow rate flow meter is a regulator such as that described with reference to FIG. 2, for example, and serves to ensure a maximum flow rate selected from the range 0.25 mm$^3$/sec to 25 mm$^3$/sec, and constant to within 1% for pressure downstream from the apparatus or device varying over the range 0 Pa to 100,000 Pa); and a reference volume 15 (or apparatus volume) of constant value and delimited by the regulator 14, the pressure sensor 13, and valves 16 and 17.

An adsorbtion isotherm is traced as follows:

Initially the bulb 12 containing the adsorbant surface is evacuated and the valve 16 is closed.

The valve 17 (leading to vacuum 18) is opened, setting up a dynamic vacuum in the reference volume 15 with an initial residual pressure Pi resulting from equilibrium between the flow of gas entering through the regulator 14 (with the pressure upstream therefrom being kept constant by an appropriate expander), and the flow of gas pumped out through the valve 17.

This pressure Pi is measured as is the temperature at which the volume 15 is maintained, and the quantity of gas initially present in the volume is deduced therefrom.

A computer memory or a graphics recorder is used for tracing the pressure signal as a function of time.

The time origin on the trace is taken as being the instant at which pumping was stopped and the valve 17 closed, at which instant adsorbtion begins by opening valve 16.

The quasi-equilibrium pressure is recorded as a function of time, i.e. as a function of the quantity of injected gas, and given the quantity of gas which is not adsorbed (and which is proportional to pressure) this record is easily converted into an adsorbtion isotherm providing an accurate measure of the quantity of gas adsorbed per gram of adsorbant material as a function of the quasi-equilibrium.

If in doubt, the validity of the selected quasi-equilibrium conditions can easily be verified by performing a second experiment at a slower adsorbtion speed (for example using a larger mass of adsorbant material). If the two adsorbtion isotherms coincide, then the "specific adsorbtion speed" is satisfactory in both cases. Otherwise it is desirable to operate at a slower speed. This shows the advantage, and indeed the necessity, of having a sonic velocity flow rate regulator available without having restrictions placed on the lowest available flow rate.

In apparatus set up as described with reference to FIG. 4, a plurality of sonic velocity flow rate regulators may be connected in parallel with respective isolation valves in order to have a plurality of injection flow rates available for performing different measurements.

An advantageous application of the apparatus described with reference to FIG. 4 is to perform rapid measurement of specific area by the nitrogen BET method using the so-called "1 point" method. Instead of determining the 3 to 5 points on the adsorbtion isotherm as generally recommended for applying the method, only one point of the isotherm is determined for an equilibrium pressure selected a priori to be close to one-third of the saturated vapor pressure of nitrogen (which is itself close to 100,000 Pa at conventional adsorbtion temperatures). Assuming both that the adsorbtion energy on the first layer is high and that the BET equation is in fact applicable over all of said first portion of the isotherm (of which only 1 point is known) a value can be determined for the specific area. This value may differ by several tens of percent from the value that would be obtained using a plurality of points on the adsorbtion isotherm, particularly when the BET equation is in fact applicable only to a limited portion of the isotherm, or when the adsorbtion energy is not much higher on the first layer than on subsequent layers (as occurs when nitrogen is adsorbed on organic polymers or when argon is adsorbed on a wide range of materials, where argon is also usable in the BET method).

In order to mitigate these limitations on the "1 point BET method" while nevertheless retaining speed, the apparatus of the invention is suitable for performing the following procedure:

The apparatus is used during preliminary testing to establish a quasi-equilibrium adsorbtion isotherm up to a pressure equal to 40% of the saturated value, with the preliminary testing being required once only for each type of adsorbant, i.e. of approximately fixed texture and chemical nature. For example silica gell having a specific area lying in the range 10 square meters per gram (m²/g) to 200 m²/g, sulfur powder having a specific area lying in the range 1 m²/g to 50 m²/g, active carbon having an apparent specific area lying in the range 200 m²/g to 800 m²/g, etc.

The validity criteria of the already-known BET equation are applied, the region to which this equation applies is determined in terms of equilibrium pressure, the quantity of gas that needs to be adsorbed to form a monolayer is deduced therefrom, and the corresponding equilibrium pressure and the slope of the adsorbant isotherm are read off from this point. These two variables are stored in memory and they are used in the following rapid procedure whenever an adsorbant of the same type is being studied.

For each new sample of the same type as above: the adsorbable gas is injected via the sonic flow rate regulator at a constant but relatively high rate until the pressure is reached at which a monolayer forms, as determined by the method described in the previous paragraph.

Injection is then stopped and the system is allowed to settle to the desired equilibrium as characterized by a predetermined value of the slope in the record of pressure as a function of time. Ideally, this slope should be zero, but time requirements lead to choosing a finite value (e.g. the pressure sensed varies by less than 1/1000-th of its value over 30 seconds). The quantity then adsorbed is generally indistinguishable from the quantity which would be adsorbed under perfect equilibrium, which is itself difficult to achieve accurately since it assumes that there is no change in temperature in the volumetric apparatus (of whatever type), no change in the level of the cryogenic bath for maintaining the temperature of the adsorbant, and no change in atmospheric pressure which could alter the boiling temperature of the bath, etc.

The quantity adsorbed at this instant is determined, with the final equilibrium pressure necessarily being slightly less than the exact pressure for forming the monolayer.

Since the slope of the adsorbtion isotherm is known, the above quantity is converted into the quantity which would be adsorbed at the exact monolayer formation pressure for a sample of the same category.

The advantages of this procedure are as follows:

by injecting the adsorbable gas at a finite flow rate (convenient orders of magnitude being 12 mm³/sec to 25 mm³/sec) the severe disturbance of equilbrium that occur in the conventional discontinuous volumetric method are avoided (and these disturbances can sometimes be partially irreversible giving rise to error and thus requiring longer periods of time for achieving equilibrium);

the small but real pressure difference from equilibrium makes it possible to stop injection at a predetermined pressure which is a little higher than the final equilibrium pressure;

as a result, in particular because of the correction that can be performed using the slope of the isotherm, the quantity of gas necessary for forming a monolayer can be determined accurately using a non-simplified version of the BET equation;

by way of comparison, it is always possible to use the simplified "1 point BET" procedure on the single point as determined above on the adsorbtion isotherm, with the limitations mentioned above; and once the adsorbant has been cooled down, a rountine experiment will typically take 5 minutes to 10 minutes for obtaining the final adsorbtion equilibrium, i.e. giving an experimental duration of about a quarter of an hour, as is expected of a quick routine measurement.

Another advantageous utilization of the regulator device of the invention concerns measuring gaseous desorbtion.

A sonic velocity flow rate regulator of the invention is used differently in a desorbtion experiment as is mainly required with nitrogen for evaluating the size distribution of mesopores (pores having openings lying in the range 2 nm to 50 nm). These pores play an important role in most technologically advantageous adsorbants (apart from molecular sieves in which all of the pores are less than 2 nm across and can therefore be studied solely from the adsorbtion branch of the isotherm). The size of the mesopores is deduced from an equation (based on Kelvin's law) relating the emptying pressure (in desorbtion) of a given category of pores to the radius of curvature of the liquid meniscus situated at the openings of the pores (providing they have previously been saturated in adsorbable material by capillary condensation).

A conventional apparatus similar to that shown diagrammatically in FIG. 4 can be used, but in this case a vacuum is permanently maintained at what used to be the upstream side 10 of the regulator 14 and is now the downstream side (or in any event when using nitrogen, a pressure of loss than 20,000 pascals is maintained). The expression given above applicable to flow rate under sonic conditions, i.e. to the maximum flow rate, now becomes:

$$(k3 \times S7 \times P11)/T1$$

and this equation shows that the flow rate continues to be proportional to the upstream pressure which is now the quasi-equilibrium pressure over the sample. When using nitrogen, the desorbtion branch differs from the adsorbtion branch only for pressures always lying between 40,000 pascals to 100,000 pascals (except for aberations that normally prevent meaningful calculation being performed of the pore size distribution). The mass flow rate obtained under sonic conditions thus varies in proportion to the quasi-equilibrium pressure. Since this pressure is recorded permanently, and since the flow rate is known at all times, the total quantity of gas remaining adsorbed on the sample situated in the bulb 12 can be deduced. Such a variable flow rate procedure is applicable to studying desorbtion because the desorbtion experiment takes place much more slowly than does an adsorbtion experiment, with the sample material being allowed to desorb through the regulator 14 until the value of the pressure inside the apparatus drops to a final pressure which is about 2.5 times smaller than the initial pressure, and this means that a desorbtion experiment may take 10 times as long in some cases.

It should be observed that flow rate is expressed in terms of mass in the equations and in terms of volume in the numerical values given, with conversion between the two being conventional and being a function of the density of the gases used, of their temperatures, and of their pressures during testing.

The present invention is not limited to the embodiments or the applications described above which are merely examples of the invention, and numerous modifications and variants can be envisaged.

We claim:

1. Apparatus comprising a gas flow regulator operating at a low flow rate and at sonic velocity and usable in any conventional equipment for measuring gaseous adsorbtion and desorbtion, the apparatus being constituted by a small section tube of ductile metal having a small portion of its length crushed in such a manner that the inside well of said tube makes contact with itself, said tube being surrounded by connection means serving both to provide sealing around the tube and to mount the tube to the said equipment for measuring gaseous adsorbtion and desorption in such a manner as to enable the tube to provide a continuous feed of gas for said equipment at a very low flow rate regardless of the back pressure therein which may vary from vacuum to at least one-tenth of the upstream feed pressure.

2. Apparatus comprising a gas flow regulator operating at a very low flow rate and at sonic velocity according to claim 1, the apparatus being wherein said very low gas flow rate has a maximum value lying in the range 0.025 mm$^3$/sec and 25 mm$^3$/sec, and wherein said value remains constant to within 1% for a downstream back pressure in said measuring equipment lying in the range 0 Pa to 100,000 Pa.

3. A method of rapidly measuring the specific area of an adsorbant material using a gas flow regulator apparatus according to claim 1, operating at a very low flow rate and at sonic velocity, and mounted in any conventional gaseous adsorption measuring equipment, wherein:

the adsorbable gas is injected into the equipment via said regulator at a constant and relatively rapid rate until the pressure, at which a monolayer forms, is reached, with this monolayer formation pressure being previously determined for said adsorbant material using a continuous adsorbtion isotherm plot obtained using said apparatus;

injection is stopped and the desired equilibrium pressure is allowed to occur, with equilibrium being characterized by a predetermined value of the slope in a record of pressure as a function of time; and the quantity adsorbed at this instant is determined and converted to the quantity which would be adsorbed at the exact monolayer formation pressure for a sample of the same category by means of the known slope of the previously obtained adsorption isotherm.

4. A method of measuring gaseous desorption using a gas flow regulator device according to claim 1 operating at a very low flow rate and at sonic velocity, and mounted in any conventional equipment comprising a bulb where a sample of adsorbing material is situated for measuring gaseous adsorption and desorbtion, wherein:

a vacuum is permanently maintained outside said regulator;

the material situated in the bulb is allowed to desorb at a very low flow rate through said regulator until the pressure inside said equipment falls to a quasi-equilibrium value of about 2.5 times less than its initial pressure; and said quasi-equilibrium internal pressure is measured on a permanent basis, and given that the mass flow rate obtained through said sonic regulator varies proportionally to said pressure in said equipment, the total quantity of gas remaining adsorbed on a sample of material is calculated.

5. A method of making a gas flow regulator that operates at a very low flow rate and at sonic velocity, the regulator being usable in any conventional equipment for measuring gaseous adsorbtion and desorbtion, operating at given utilization pressures, and into which a gas is to be injected at a selected very low flow rate, the method comprising the following steps:

a small section tube of ductile metal is taken having a wall thickness which is sufficient to withstand said various utilization gas pressures;

said tube is mounted on connection means serving both to provide sealing around the tube and also to enable it to be mounted on said equipment, said means being mounted close to an end of said tube and at a sufficient distance therefrom to enable the following operations to be performed, which operations may alternatively be performed prior to mounting the tube in the connection means;

a short length of said tube is crushed between said connection means and the above-mentioned corresponding end;

said connection means is connected together with the tube to a known calibrated volumetric measuring apparatus, and a gas is applied at one end of the tube at a given calibration pressure, and the increase in pressure in a known volume into which other end of the tube opens out is measured with the initial pressure of the volume being selected as a function of a downstream pressure range for which the sonic flow control must be calibrated and of the upstream pressure of the applied gas; and the flow rate obtained in this way is determined on a continuous basis and it is verified that the flow rate is constant and corresponds to not more than a desired very low flow rate for which the sonic flow control must be calibrated over the entire desired range of variation in downstream pressure during measurement, and if the verification fails the crushing operation is continued by slightly increasing the extent to which the tube is pinched, and calibration is verified again until a flow rate is obtained which is no greater than the desired flow rate given said initially selected upstream and downstream pressures.

6. A method of making a regulator according to claim 5, wherein said tube is crushed by clamping means constituted on one side by a ball whose diameter is greater than the width of said tube and on the other side by an anvil against which said tube is placed and subsequently pinched by the ball which is moved towards the anvil until a distance is reached which corresponds to the desired sonic flow rate of the gas flow regulator.

7. A method of making a regulator according to claim 5, wherein said tube is crushed by clamping means constituted on one side by a roller and on the other side by any surface suitable for constituting an abutment and whose intersection with the plane containing the axis of said roller and containing the displacement direction for performing the crushing operation is a convex line whose radius of curvature is greater than the radius of curvature of said tube.

8. A method of making a regulator according to claim 5, wherein said tube is crushed by clamping means constituted on one side by a prism and on the other side by any surface suitable for constituting an anvil and whose intersection with the plane including the edge of said prism and including the direction in which the displacement for obtaining crushing takes place is a convex line whose radius of curvature is greater than the radius of curvature of said tube.

9. A method of making a regulator according to claim 5, wherein the desired sonic flow rate lies in the range of 0.025 mm$^3$/sec to 25 mm$^3$/sec, in that the flow rate remains constant to within 1% for the downstream pressure varying over the range 0 Pa to 100,000 Pa.

10. A method of making a regulator according to claim 5, wherein the desired sonic flow rate is 0.025 mm$^3$/sec, and wherein it remains constant to within 0.5% for a selected upstream utilization pressure of 350,000 Pa, and for a downstream pressure varying over the range 0 Pa to 30,000 Pa.

* * * * *